United States Patent [19]

Iimuro et al.

[11] Patent Number: 4,950,807

[45] Date of Patent: Aug. 21, 1990

[54] PROCESS FOR PREPARING BISPHENOL A

[75] Inventors: Shigeru Iimuro; Yoshio Morimoto; Takashi Kitamura, all of Aichi, Japan

[73] Assignee: Mitsui Toatsu Chemicals, Inc., Tokyo, Japan

[21] Appl. No.: 308,667

[22] Filed: Feb. 10, 1989

[30] Foreign Application Priority Data

Feb. 17, 1988 [JP] Japan ................................ 63-32838

[51] Int. Cl.$^5$ ........................ C07C 37/20; C07C 37/70
[52] U.S. Cl. ................................ 568/727; 568/724; 568/722
[58] Field of Search ............... 568/724, 727, 749, 722, 568/723, 751, 753

[56] References Cited

U.S. PATENT DOCUMENTS

| 3,073,868 | 1/1963 | Prahl | 568/727 |
| 4,375,567 | 3/1983 | Faler | 568/727 |
| 4,507,509 | 3/1985 | Mendiratta et al. | 568/724 |
| 4,517,387 | 5/1985 | Matsunaga et al. | 568/728 |

FOREIGN PATENT DOCUMENTS

| 0045959 | 2/1982 | European Pat. Off. | 568/727 |
| 0112615 | 7/1984 | European Pat. Off. | 568/727 |
| 2048661 | 4/1972 | Fed. Rep. of Germany | 568/724 |
| 227697 | 9/1985 | Fed. Rep. of Germany | 568/727 |
| 928329 | 6/1963 | United Kingdom | 568/724 |
| 1081257 | 6/1966 | United Kingdom | 568/724 |
| 1377227 | 12/1974 | United Kingdom | 568/724 |

Primary Examiner—Werren B. Lone
Attorney, Agent, or Firm—Burns, Doane, Swecker & Mathis

[57] ABSTRACT

A process for producing high-purity bisphenol A comprises reacting phenol with acetone in the presence of an acid catalyst to obtain a product mixture, removing the acid catalyst from the product mixture, thereby yielding a liquid mixture, treating the liquid mixture with a weakly basic ion-exchange resin having pyridyl groups as the exchange groups, and purifying the treated liquid mixture. The process does not cause any corrosion of equipment and any decomposition and discoloration of bisphenol A during distillation.

6 Claims, No Drawings

PROCESS FOR PREPARING BISPHENOL A

BACKGROUND OF THE INVENTION

The present invention relates to a process for preparing high-purity 2,2-bis(4-hydroxyphenyl)propane (referred to as bisphenol A hereinafter).

Bisphenol A is used as a raw material for polycarbonate resins and epoxy resins and also for engineering plastics recently. Colorless and high-purity bisphenol A is required for these uses.

Bisphenol A is prepared by the reaction of acetone with excess phenol in the presence of an acidic catalyst. The product mixture contains bisphenol A and also the catalyst, unreacted acetone, unreacted phenol, water, and other by-products such as coloring substances.

Inorganic acids such as hydrochloric acid and strongly acidic ion-exchange resins are known as the catalyst for the reaction.

There are many known processes for obtaining high-purity bisphenol A from the product mixture. For example, in the case where hydrochloric acid has been used as the catalyst in the reaction, the product mixture is heated at 110° to 120° C. under reduced pressure, thereby removing hydrochloric acid, unreacted acetone, water, and a small amount of phenol, and thereafter bisphenol A in the form of an adduct with phenol is separated by cooling. The other process includes distillation to separate bisphenol A from other substances having a higher and lower boiling point than that of bisphenol A. The thus-obtained bisphenol A may be further purified by extraction with a solvent or recrystallization from a solution.

In the case where hydrochloric acid has been used as the catalyst, the product mixture which has been distilled to remove hydrochloric acid, acetone and water, still contains a trace amount of hydrochloric acid which causes some trouble in the subsequent purification steps.

One of the trouble is the corrosion of equipment due to the acid. The corrosion yields metal salts which contaminate bisphenol A, and the removal of the metal salts requires a complicated purification procedure. A possible countermeasure is to use equipment made of an acid-resistant material; however, this is not economical because such equipment is expensive.

Another trouble is that bisphenol A is decomposed due to the acidic substance during distillation, as described in U.S. Pat. 3,073,868 and Japanese Patent Publication No. 4875/1963.

The process in which a strongly acidic ion-exchange resin is used as the catalyst is more favorable than the process in which hydrochloric acid is used as the catalyst because the ion-exchange resin is separated more easily. However, in the case where the reaction is carried out at 70° to 100° C., the product mixture also contains a trace amount of free acid originating from the exchange groups which are eliminated.

GB Patent No. 1,377,227 and Japanese Patent Laid-open No. 1543/1974 disclose that bisphenol A can be distilled without any decomposition, if the distillation is conducted after the adduct of bisphenol A with phenol is melted and the melt is treated with an acidic or weakly basic ion-exchange resin. However, heating above 90° C. is necessary for melting the adduct of bisphenol A with phenol. Therefore, a weakly basic ion-exchange resin having exchange groups of secondary or tertiary amine is not suitable for treating the melt, because the ion-exchange resin can not withstand temperatures above 70°–80° C. for a long period of time. At temperatures above that limit, the exchange groups are eliminated from the weakly basic ion-exchange resin and the eliminated exchange groups discolor the treated solution with a color between yellow and red.

SUMMARY OF THE INVENTION

It is an object of the present invention to provide a process for producing high-purity bisphenol A without causing the above-mentioned troubles, i.e., the corrosion of equipment due to a trace amount of acid and the decomposition of bisphenol A that takes place during distillation.

To achieve the aforesaid object, we carried out a series of experiments, which led to the finding that high-purity bisphenol A can be obtained by removing the acid catalyst from the product mixture, treating the product mixture with a specific weakly basic ion-exchange resin, and thereafter purifying the product mixture in the usual process. The present invention was completed on the basis of this finding.

In accordance with the present invention, there is provided a process for producing high-purity bisphenol A which comprises reacting phenol with acetone in the presence of an acid catalyst to obtain a product mixture, removing the acid catalyst from the product mixture, thereby yielding a liquid mixture, treating the liquid mixture with a weakly basic ion-exchange resin having pyridyl groups as the exchange groups, and purifying the treated liquid mixture.

DETAILED DESCRIPTION OF THE INVENTION

According to the process of the present inveniton, the molar ratio of phenol to acetone in the starting mixture is from 4:1 to 12:1 usually and the reaction temperature is 40 to 100° C.

According to the process of the present inveniton, an inorganic acid such as hydrochloric acid, or a strongly acidic cation-exchange resin is used as the catalyst.

The reaction yields a product mixture containing bisphenol A, and also unreacted phenol, unreacted acetone, acid catalyst, water, and by-products.

In the case of using hydrochloric acid, in the reaction the product mixture is distilled under reduced pressure to remove water, acetone, hydrochloric acid, and a small amount of phenol. The vacuum distillation should be performed preferably at a pressure of 20 to 200 mm Hg and a temperature of 90° to 150° C. After the distillation, there is obtained a liquid mixture.

In the case of using a strongly acidic cation-exchange resin, in the reaction the product mixture is separated from the cation-exchange resin, and the product mixture is distilled under reduced pressure to remove water, acetone, and a small amount of phenol. The vacuum distillation should be performed preferably at a pressure of 50 to 300 mm Hg and a temperature of 70° to 120° C. After the distillation, there is obtained a liquid mixture.

The thus-obtained liquid mixture contains bisphenol A, phenol, and a trace amount of acid (usually smaller than 2 equivalents of acid per ton of the liquid mixture, preferably smaller than 1 equivalent per ton of the liquid mixture). For the removal of this acid in trace amounts, the liquid mixture is treated with a weakly basic ion-exchange resin having pyridyl groups as the exchange groups, according to the process of the present invention.

The weakly basic ion-exchange resins that can be used in the process of the present invention include, for example, a copolymer of 2-vinylpyridine and/or 4-vinylpyridine and divinylbenzene, and a copolymer of 2-vinylpyridine and/or 4-vinylpyridine, divinylbenzene, and styrene. These ion-exchange resins can be used at high temperatures up to 150° C.

According to the process of the present invention, the treatment of the liquid mixture with the weakly basic ion-exchange resin may be carried out continuously or batchwise at 70° to 150° C. For continuous treatment, the liquid mixture should preferably be fed at a flow rate of 10 to 1000 kg/hr for 1 kg of the weakly basic ion-exchange resin. For batchwise treatment, the liquid mixture should preferably be mixed with 1 to 20 wt % of the weakly basic ion-exchange resin, and they should be kept in contact with each other for 5 to 60 minutes.

The treated liquid mixture is separated from the weakly basic ion-exchange resin. The separated liquid mixture is free of acid and therefore can undergo the ordinary purification step without any corrosion of equipment and any decomposition of bisphenol A, and there is obtained high-purity bisphenol A.

For purification, the liquid mixture which has undergone dehydrochlorination as mentioned above is cooled so that bisphenol A crystallizes out in the form of an adduct of bisphenol A with phenol. The crystals are separated, and bisphenol A is obtained by removing phenol from the adduct. Alternatively, the liquid mixture which has undergone dehydrochlorination is freed of phenol, followed by distillation. The distilled bisphenol A is further purified by recrystallization from a solution.

EXAMPLES

The invention will be described in more detail with reference to the following examples, in which "%" means "wt %", unless otherwise indicated.

EXAMPLE 1

Condensation of phenol (564 g, 6 mol) and acetone (58 g, 1 mol) was carried out at 50° in the presence of hydrochloric acid as the catalyst. The product mixture was distilled under reduced pressure (with the final pressure being 70 mm Hg) at 120° C. to remove hydrochloric acid, water, acetone, and a small amount of phenol. The distillation residue contained hydrochloric acid in an amount of 0.25 equivalents per ton.

The distillation residue was subsequently mixed with 5% of weakly basic ion-exchange resin having pyridyl groups as the exchange groups ("KEX-212" made by Koei Kagaku Kogyo Co., Ltd.) and stirred at 120° C. for 15 minutes. The ion-exchange resin was filtered off. The resulting filtrate contained no detectable amount of hydrochloric acid.

The filtrate was freed of phenol by vacuum distillation (with the final pressure being 10 mm Hg) at 170° C. Finally, there was obtained white pure bisphenol A by distillation. During the distillation, bisphenol A did not decompose.

COMPARATIVE EXAMPLE 1

The same procedure as in Example 1 was repeated to produce bisphenol A, except that the weakly basic ion-exchange resin ("KEX-212") was not used. The distillation residue contained hydrochloric acid in an amount of 0.27 equivalents per ton. In the distillation of bisphenol A, some decomposition of bisphenol A occurred, discoloring the distilled bisphenol A yellow.

EXAMPLE 2

The same procedure as in Example 1 was repeated up to the step of treatment with the weakly basic ion-exchange resin ("KEX-212") to produce bisphenol A. The distillation residue contained hydrochloric acid in an amount of 0.27 equivalents per ton. After the treatment with "KEX-212", the filtrate contained no detectable amount of hydrochloric acid.

To the liquid treated as mentioned above was added 3% of water. The liquid was stirred in a stainless steel vessel under an atmosphere of nitrogen at 120° C. for 48 hours. Then, the liquid was cooled to 45° C. for crystallizing the adduct of bisphenol A with phenol. The adduct was filtered off, followed by rinsing with an equal amount of phenol. The thus-obtained adduct produced a Hazen color of 5 APHA when 20 g of the adduct was dissolved in 20 ml of ethanol.

COMPARATIVE EXAMPLE 2

The same procedure as in Example 2 was repeated to produce bisphenol A, except that the weakly basic ion-exchange resin ("KEX-212") was not used. The distillation residue contained hydrochloric acid in an amount of 0.20 equivalents per ton. The adduct obtained after crystallization produced a Hazen color of 30 APHA when 20 g of the adduct was dissolved in 20 ml of ethanol, although there was no visually noticeable corrosion in the stainless steel vessel used.

COMPARATIVE EXAMPLE 3

The same procedure as in Example 2 was repeated to produce bisphenol A, except that the weakly basic ion-exchange resin ("KEX-212") was replaced by a weakly basic ion-exchange resin having tertiary amine groups as the exchange groups ("LEWATIT MP-62" made by Bayer AG). The distillation residue contained hydrochloric acid in an amount of 0.20 equivalents per ton. After the treatment with "MP-62", the filtrate contained no detectable amount of hydrochloric acid, but assumed a red color. The adduct obtained after crystallization produced a Hazen color of 50 APHA when 20 g of the adduct was dissolved in 20 ml of ethanol.

EFFECTS OF THE INVENTION

According to the process of the present invention, the product mixture is freed of hydrochloric acid almost completely and the bisphenol A free of hydrochloric acid can be distilled at high temperatures without any decomposition. In addition, it is possible to prevent bisphenol A from being contaminated by the corrosion of equipment. Thus it is possible to produce colorless and high-purity bisphenol A.

What is claimed is:

1. A process for producing high-purity bisphenol A which comprises reacting phenol with acetone in the presence of an acid catalyst to obtain a product mixture containing bisphenol A as a separate compound, removing the acid catalyst from the product mixture, thereby yielding a liquid mixture, treating the liquid mixture with a weakly basic ion-exchange resin having pyridyl groups as the exchange groups, and purifying the treated liquid mixture to obtain the high-purity bisphenol A.

2. A process as claimed in claim 1, wherein the molar ratio of phenol to acetone in the starting mixture is from 4:1 to 12:1 and the reaction temperature is 40° to 100° C.

3. A process as claimed in claim 1, wherein the acid catalyst is one member selected from the group consisting of hydrochloric acid and strongly acidic cation-exchange resin.

4. A process as claimed in claim 1, wherein the weakly basic ion-exchange resin having pyridyl groups as the exchange groups is one member selected from the group consisting of a copolymer of 2-vinylpyridine and/or 4-vinylpyridine and divinylbenzene, and a copolymer of 2.vinylpyridine and/or 4-vinylpyridine, divinylbenzene, and styrene.

5. A process as claimed in claim 1, wherein the treatment of the liquid mixture with the weakly basic ion-exchange resin is carried out continuously by feeding the liquid mixture at a flow rate of 10 to 1000 kg/hr for 1 kg of the weakly basic ion-exchange resin.

6. A process as claimed in claim 1, wherein the treatment of the liquid mixture with the weakly basic ion-exchange resin is carried out batchwise by mixing the liquid mixture with 1 to 20 wt % of the weakly basic ion-exchange resin.

* * * * *